United States Patent [19]

Nonn et al.

[11] 4,280,960
[45] Jul. 28, 1981

[54] PHOSPHONIC ACID ESTERS

[75] Inventors: Konrad Nonn; Klaus Walz; Karlheinz Wolf; Günther Boehmke, all of Leverkusen, Fed. Rep. of Germany

[73] Assignee: Bayer Aktiengesellschaft, Leverkusen, Fed. Rep. of Germany

[21] Appl. No.: 96,725

[22] Filed: Nov. 23, 1979

[30] Foreign Application Priority Data

Dec. 14, 1978 [DE] Fed. Rep. of Germany ....... 2853936

[51] Int. Cl.$^3$ .......................... C07F 9/40; C04B 30/02
[52] U.S. Cl. ..................................... 260/403; 260/928; 260/929; 260/982; 260/978; 252/351; 106/288 Q; 106/302; 106/300; 106/304; 106/308 Q
[58] Field of Search ................................ 260/929, 403

[56] References Cited

U.S. PATENT DOCUMENTS

| 3,578,731 | 5/1971 | Mange et al. | 260/929 |
| 3,956,431 | 5/1976 | Honig et al. | 260/929 |

Primary Examiner—Anton H. Sutto
Attorney, Agent, or Firm—Sprung, Felfe, Horn, Lynch & Kramer

[57] ABSTRACT

Phosphonic acid esters of the general formula

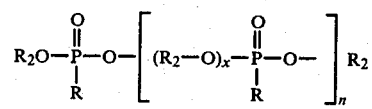

in which

R represents a $C_{12}$-$C_{22}$-alkyl or-alkenyl radical, a $C_7$—$C_{18}$-aralkyl radical or a radical of the formula —$R_4$—O—CO—$R_5$ or —$R_4$—COO—$R_5$, wherein $R_4$ denotes an optionally substituted $C_2$—$C_4$-alkylene radical and $R_5$ denotes a $C_6$—$C_{22}$-alkyl or -alkenyl radical or a cycloalkyl radical, $R_1$ represents the ethylene and/or 1,2-propylene radical, $R_2$ represents hydrogen, $C_1$—$C_4$-alkyl or —$(R_1$—$O)_{x-1}R_1$—$R_3$, $R_3$ represents OH, Cl or Br, x represents an integer from 2 to 100 and
n represents a number from 1 to 10, are used, especially in aqueous formulations, as emulsifying agents and dispersing agents.

1 Claim, No Drawings

PHOSPHONIC ACID ESTERS

The invention relates to phosphonic acid esters of the general formula

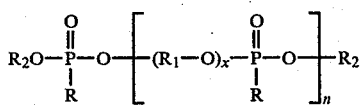

in which

R represents a $C_{12}$—$C_{22}$—alkyl or -alkenyl radical, a $C_7$—$C_{18}$-aralkyl radical or a radical of the formula —$R_4$—O—CO—$R_5$ or —$R_4$—COO—$R_5$, wherein $R_4$ denotes an optionally substituted $C_2$—$C_4$—alkylene radical and $R_5$ denotes a $C_6$—$C_{22}$—alkyl or -alkenyl radical or a cycloalkyl radical, $R_1$ represents the ethylene and/or 1,2-propylene radical, $R_2$ represents hydrogen, $C_1$—$C_4$—alkyl or —$(R_1$—O$)_{x-1}R_1$—$R_3$, $R_3$ represents OH, Cl or Br, x represents an integer from 2 to 100 and n represents a number from 1 to 10, a process for their preparation, their use as emulsifying agents and dispersing agents, and formulations, in particular aqueous dyestuff formulations, containing them.

Cycloalkyl is understood, in particular, as cyclopentyl, cyclohexyl and tetrahydronaphthyl and derivatives thereof substituted by $C_1$—$C_4$ —alkyl. Examples of suitable aralkyl radicals are the benzyl or phenylethyl radical and derivatives thereof substituted in the benzene ring by $C_1$—$C_{12}$—alkyl radicals, such as the methylbenzyl or dodecylbenzyl radical. Substituents of the radical $R_4$ which may be mentioned are, in particular, the radicals —COOR$_5$ or —CH$_2$OCO—R$_5$, R$_5$ having the abovementioned meaning. Examples of radicals R which may be mentioned are the n-dodecyl, n-tetradecyl, n-hexadecyl, n-octadecyl, n-eicosyl, n-behenyl, undecenyl or oleyl radical. Examples of radicals $R_4$ which may be mentioned are the methylene, 1,1-ethylene, 1,2-ethylene, 1,2-propylene, 1,3-propylene, 1,1-isobutylene, 1,2-butylene or 1,4-butylene radical.

Examples of suitable radicals R$_5$ are the n-hexyl, n-octyl, n-decyl, n-undecyl, n-dodecyl, n-pentadecyl, n-heptadecyl, n-octadecyl, 2-ethylhexyl, undecenyl, heptadecenyl or octadecenyl radical, or a cyclohexyl, tetrahydronaphthyl or abietyl radical which is optionally substituted by $C_1$—$C_4$—alkyl.

The phosphonic acid esters of the formula I according to the invention are prepared by a process in which lower alkyl esters, aryl esters or halides of phosphonic acid of the formula

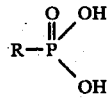

in which

R has the meaning indicated for formula I, are reacted with polyglycol compounds of the formula HO—$(R_1$—O$)_x$—H (III) 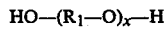

and, if appropriate, polyglycol compounds of the formula

Hal—$(R_1$—O$)_x$—H (IIIa) 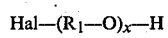

in which $R_1$ and x have the meaning indicated for formula (I) and

Hal represents chlorine or bromine, or lower alkyl esters of the phosphonic acids of the formula (II) are reacted with compounds of the formula Hal—$(R_1$—O$)_{x-1}$—$R_1$—Hal (IV) 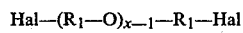

wherein $R_1$ and x have the meaning indicated for formula (I) and

Hal represents chlorine or bromine.

Lower alkyl esters are understood as the methyl, ethyl, propyl, isopropyl, butyl or isobutyl ester, in particular the methyl or ethyl ester. Suitable aryl esters are, in particular, the phenyl or cresyl ester. Possible acid halides of phosphonic acids of the formula (II) are, in particular, the chlorides or bromides.

The reaction is appropriately carried out by a procedure in which the lower alkyl esters or aryl esters of the phosphonic acids of the formula (II) and the compounds of the formula (III) are mixed in a molar ratio of 1:0.5 to 1:3, preferably 1:0.8 to 1:1.6, and the mixture is heated to temperatures of 150°–220° C., preferably 170°–200° C. The lower alcohol or the phenol formed is removed continuously from the reaction mixture, if necessary under a vacuum. A corresponding procedure is followed if halogen compounds of the formula (IV) are employed instead of the hydroxy compounds of the formula (III). Alkyl halides formed are likewise distilled off continuously from the reaction mixture. Catalysts or solvents, such as alcoholates, triphenylphosphine or dimethylformamide, can be added to accelerate the reaction.

The phosphonic acid esters of the formula (I) according to the invention can also be prepared by a process in which chlorides or bromides of the phosphonic acids of the formula (II) are reacted with the compounds of the formula (III) at 20°–200° C., preferably 20°–120° C. If appropriate, the reaction can be carried out in the presence of acid-binding agents and/or inert organic solvents.

Examples which may be mentioned of the phosphonic acids of the formula (II) on which the phosphonic acid esters of the formula (I) according to the invention are based are: 1-dodecanephosphonic acid, 1-tetradecanephosphonic acid, 2-tetradecanephosphonic acid, 1-octadecanephosphonic acid, 1-eicosanephosphonic acid, 1-octadecenephosphonic acid, benzylphosphonic acid, phenylethylphosphonic acid, butylbenzylphosphonic acid, dodecylbenzylphosphonic acid, 2-octanoyloxyethane-1-phosphonic acid, 2-dodecanoyloxyethane-1-phosphonic acid, 2-hexadecanoyloxyethane-1-phosphonic acid, 2-octadecanoyloxyethane-1-phosphonic acid, 2-eicosanoyloxyethane-1-phosphonic acid, 2-octadecenoyloxyethane-1-phosphonic acid, 2-dodecanoyloxypropane-1-phosphonic acid, 3-dodecanoyloxypropane-1-phosphonic acid, 2,2-bis-(dodecanoyloxymethyl)ethane-1-phosphonic acid, 2-octyloxycarbonyl-ethane-1-phosphonic acid, 2-dodecyloxycarbonyl-ethane-1-phosphonic acid, 2- octadecyloxycarbonyl-ethane-1-phosphonic acid, 2-eicosyloxycarbonyl-ethane-1-phosphonic acid, 2-octadecenyloxycarbonyl-ethane-1-phosphonic acid, 2-dodecyloxycarbonylpropane-1-phosphonic acid, 2,3bis-(decyloxycarbonyl)-propane-1-phosphonic acid and 2,3-bis-(dodecyloxycarbon-yl)-propane-1-phosphonic acid.

Examples of suitable polyglycol compounds of the formula (III) are diethylene glycol, tetraethylene glycol, hexaethylene glycol, octaethylene glycol, dodecaethylene glycol, tripropylene glycol and reaction products of tripropylene glycol with 8 or 12 mols of ethylene oxide.

Preferred compounds according to the invention are prepared by a process in which dimethyl or diethyl esters of phosphonic acids of the formula

in which
R has the abovementioned meaning and
$R_6$ represents methyl or ethyl,
are reacted with polyglycol ethers of the formula

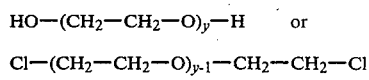

wherein
y represents an integer from 2 to 50, in particular from 4 to 20.

Particularly preferred compounds are obtained when dimethyl or diethyl esters of phosphonic acids of the formula

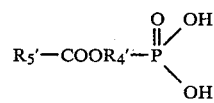

in which
$R_4'$ represents $C_2$—$C_4$-alkylene and
$R_5'$ represents $C_{11}$—$C_{17}$-alkenyl,
are employed.

Preferred dyestuff formulations according to the invention are aqueous dispersions which contain water-insoluble dyestuffs and phosphonic acid esters of the formula (I). They are used for pigmenting natural and synthetic materials.

Preferred possible water-insoluble dyestuffs are pigments, but also disperse dyestuffs and optical brighteners.

Pigments which can be used are organic pigments, for example pigments of the azo, anthraquinone, azaporphine, thioindigo or polycyclic series of quinacridone, dioxazine, naphthalenetetracarboxylic acid or perylenetetracarboxylic acid pigments, such as are known from the Colour Index, 3rd edition (1971), volume 3, pages 3272-3390, and in particular inorganic pigments, such as zinc sulphides, cadmium sulphides or selenides, ultramarine, titanium dioxide, iron oxides, nickel or chromium titanium yellow, chromium oxides, chromate pigments and carbon black, as well as mixtures thereof.

The disperse dyestuffs belong, for example, to the azo, anthraquinone, methine, quinophthalone or amino-coumarin series, such as are listed in the Colour Index, 3rd edition (1971), volume 2, pages 2483-2741.

Optical brighteners which are sparingly soluble in water belong, for example, to the coumarin, stilbene, naphthalimide or carbostyryl series.

Further water-insoluble dyestuffs which may be mentioned are those which sublime at 160°-220° C. and are customarily used in transfer printing, as well as sublimable carbinol bases and carbinol base derivatives of cationic dyestuffs.

The dyestuff dispersions according to the invention contain 20-75%, preferably 30-70%, of dyestuff, 1-20%, preferably 2-10%, of phosphonic acid ester, 0-20%, preferably 2-10%, of non-ionic and/or anionic surface-active agents 0-25% of water-retention agents, such as polyglycols, 0-2% of preservatives, such as agents which split off formaldehyde, and 3-50% of water, the numerical data relating to the dyestuff dispersion.

EXAMPLE 1

308 parts of 2-lauroyloxy-ethanephosphonic acid dimethyl ester and 337 parts of octaethylene glycol are mixed and the mixture is heated to 160° C. under a vacuum of 90-100 mm Hg in the course of 1 hour. The methanol which forms is distilled off over a condenser into a receiver which is cooled with ice. As the splitting off of methanol decreases, the temperature is slowly increased to 180°-185° C. and the batch is kept at this temperature for 10 hours. After cooling, 580 parts of a phosphonic acid ester which is soluble in water giving a clear solution is obtained as a pale yellow liquid. P content: 4.8%; molecular weight: 1,150; surface tension of a 0.1% strength aqueous solution: 31 dynes/cm; $n_D^{20}$: 1.4643.

EXAMPLE 2

752 parts of 2-octadecenoyloxy-ethanephosphonic acid dimethyl ester and 663 parts of octaethylene glycol are reacted at 180°-185° C. in the manner indicated in Example 1. 1,140 parts of a phosphonic acid ester are obtained as a water-soluble, brown liquid. P content: 3.9%; $n_D^{20}$: 1.4698; surface tension of a 0.1% strength aqueous solution: 37.5 dynes/cm.

EXAMPLE 3

102 parts of 1-dodecanephosphonic acid dimethyl ester are reacted with 123 parts of octaethylene glycol at 180°-200° C. in the manner described in Example 1. 210 parts of a water-soluble phosphonate are obtained as a yellow liquid.

P content: 5.2%; surface tension of a 0.1% strength aqueous solution: 33.0 dynes/cm.

EXAMPLE 4

508 parts of phosphonosuccinic acid tetramethyl ester, 372 parts of dodecyl alcohol and 740 parts of oxtaethylene glycol are mixed and the mixture is heated slowly to 160°-170° C. 165 parts of methanol are then distilled off under reduced pressure (90-100 mm Hg) in the course of 12 hours, during which the temerature is increased to 180°-185° C. 1,450 parts of a water-soluble phosphonic acid ester are obtained as a light brown liquid.

P content: 4.8%; $n_D^{20}$: 1.4666; surface tension of a 0.1% strength aqueous solution: 32.0 dynes/cm.

EXAMPLE 5

162 parts of 2-lauroyloxy-ethanephosphonic acid dimethyl ester and 196 parts of a polyglycol ether which has been prepared by replacing the terminal hydroxyl groups of octaethylene glycol by chlorine with the aid of thionyl chloride are mixed with 75 parts of dimethylformamide and the mixture is heated to 160°–170° C. for 20 hours. The methyl chloride which forms is removed continuously from the reaction mixture. All the volatile constituents are then removed under 2 mm Hg. 349 parts of a water-soluble phosphonic acid ester are obtained as a dark brown liquid.

P content: 4.4%; molecular weight: 1,100.

EXAMPLE 6

336 parts of 2-lauroyloxy-ethanephosphonic acid dimethyl ester and 546 parts of dodecaethylene glycol are reacted in the manner described in Example 1. 827 parts of phosphonic acid ester which dissolves in water giving a clear solution are obtained as a brown, viscous liquid.

P content: 3.9%; $n_D^{20}$: 1.4677; surface tension of a 0.1% strength aqueous solution: 31 dynes/cm.

EXAMPLE 7

268 parts of oleyl alcohol, 254 parts of phosphonosuccinic acid tetramethyl ester and 370 parts of octaethylene glycol are reacted in the manner described in Example 4. 780 parts of a water-soluble phosphonic acid ester are obtained as a brown, viscous liquid.

P content: 3.9%; $n_D^{20}$: 1.4708; surface tension of a 0.1% strength aqueous solution: 38.5 dynes/cm.

EXAMPLE 8

A mixture consisting of 57% by weight of iron oxide yellow pigment, which predominantly contains precipitated iron hydroxide of the goethite type, 4% by weight of the phosphonate prepared according to Example 1, 2% by weight of an addition product of nonylphenol and 7 mols of ethylene oxide, 1% by weight of sodium ligninsulphonate, 0.2% by weight of sodium pentachlorophenate, 15% by weight of ethylene glycol and 20.8% by weight of water is homogenised with a high-speed stirrer. The mixture is then ground on a uniroll mill. A yellow pigment dispersion which is capable of flow and can easily be dispersed in aqueous emulsion paints is obtained.

EXAMPLE 9

A mixture of 70% by weight of titanium dioxide pigment (rutile type), 5% by weight of the phosphonate prepared according to Example 1, 0.5% by weight of a high-molecular silica acid, to prevent sedimentation of the pigment in the paste, 0.2% by weight of sodium pentachlorophenate, 15% by weight of ethylene glycol and 9.3% by weight of water are worked into a slurry in a dissolver. After the white dispersion, which is capable of flow, has been stored at room temperature for six months, no formation of pigment agglomerates is observed. The products described in Examples 2, 5, 6 or 7 can be used instead of the phosphonate according to Example 1 with similar success.

EXAMPLE 10

A mixture of 71% by weight of chromium oxide green pigment, 4% by weight of the phosphonate prepared according to Example 3, 1.5% by weight of sodium ligninsulphonate, 0.2% by weight of sodium pentachlorophenate, 10% by weight of ethylene glycol and 13.3% by weight of water is ground as in Example 8. A green dispersion which can readily be dispersed in commercially available, aqueous exterior wall paints by stirring is obtained.

EXAMPLE 11

A mixture of 35% by weight of carbon black, 10% by weight of the phosphonate prepared according to Example 2, 0.2% by weight of sodium pentachlorophenate, 15% by weight of ethylene glycol and 39.8% by weight of water is homogenised with a high-speed stirrer and is then ground in a high-speed stirred ball mill with glass beads 0.3–0.4 mm in diameter until the particle size is less than $2\mu$. The black, intensely colored dispersion is outstandingly suitable for tinting or dulling aqueous emulsion paints.

EXAMPLE 12

A mixture of 40% by weight of C. I. Pigment Yellow 3 (C. I. 11,710), 8% by weight of the phosphonate prepared according to Example 4, 5% by weight of an adduct of nonylphenol and 10 mols of ethylene oxide, 0.4% by weight of sodium pentachlorophenate, 20% by weight of ethylene glycol and 26.6% by weight of water is ground in a stirred ball mill as in Example 11. This yellow pigment dispersion, in which no sediment forms, is outstandingly suitable for tinting white, aqueous emulsion paints such as are used for painting the insides of buildings.

We claim:
1. Phosphonic acid esters of the general formula

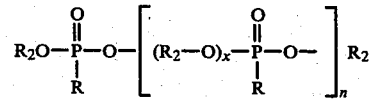

in which
R represents a $C_{12}$—$C_{22}$—alkyl or -alkenyl radical, a $C_7$—$C_{18}$—aralkyl radical or a radical of the formula —$R_4$—O—CO—$R_5$ or —$R_4$—COO—$R_5$, wherein
$R_4$ denotes an optionally substituted $C_2$—$C_4$—alkylene radical and
$R_5$ denotes a $C_6$—$C_{22}$—alkyl or -alkenyl radical or a cycloalkyl radical,
$R_1$ represents the ethylene and/or 1,2-propylene radical,
$R_2$ represents hydrogen, $C_1$—$C_4$—alkyl or —($R_1$—O)$_{x-1}$$R_1$—$R_3$,
$R_3$ represents OH, Cl or Br,
x represents an integer from 4 to 50 and
n represents a number from 1 to 10.

* * * * *

UNITED STATES PATENT AND TRADEMARK OFFICE
CERTIFICATE OF CORRECTION

PATENT NO. : 4,280,960
DATED : Jul. 28, 1981
INVENTOR(S) : Konrad Nonn et al

It is certified that error appears in the above-identified patent and that said Letters Patent are hereby corrected as shown below:

Column 6, line 44    Delete "$R_2$" second occurence and insert --$R_1$--.

Signed and Sealed this

Fifth Day of January 1982

[SEAL]

Attest:

GERALD J. MOSSINGHOFF

Attesting Officer    Commissioner of Patents and Trademarks